United States Patent [19]
Gevins et al.

[11] Patent Number: 5,513,649
[45] Date of Patent: May 7, 1996

[54] ADAPTIVE INTERFERENCE CANCELER FOR EEG MOVEMENT AND EYE ARTIFACTS

[75] Inventors: Alan S. Gevins; Weixiu Du, both of San Francisco; Harrison Leong, Richmond, all of Calif.

[73] Assignee: SAM Technology, Inc., San Francisco, Calif.

[21] Appl. No.: 216,256

[22] Filed: Mar. 22, 1994

[51] Int. Cl.⁶ .................................................. A61B 5/0476
[52] U.S. Cl. ............................................................. 128/731
[58] Field of Search .............................. 128/731–3, 715, 128/687, 774, 782, 745

[56] References Cited

U.S. PATENT DOCUMENTS

| | | | |
|---|---|---|---|
| 3,774,593 | 11/1973 | Hakata et al. | 128/731 |
| 4,171,696 | 10/1979 | John | 128/731 |
| 4,417,592 | 11/1983 | John | 128/731 |
| 4,781,200 | 11/1988 | Baker | 128/775 X |
| 5,140,992 | 8/1992 | Zuckerwar et al. | 128/715 |

Primary Examiner—Angela D. Sykes
Attorney, Agent, or Firm—Eliot S. Gerber

[57] ABSTRACT

In an EEG (electroencephalogram) system to detect brain waves from a subject, the adverse effect on the EEG recording of artifact due to head, body and eye movements is reduced. A head and body movement reference signal can be provided by an accelerometer, motion detector or, alternatively, spatial average of EEG channels. Eye motion sensors are used as a reference for eye movement artifacts. A composite reference signal consists of the head, body and eye movement reference signals. The contaminated EEG is the primary input to the adaptive movement and eye artifact canceler, in which an adaptive filter estimates the contaminants in the measured EEG data, and then subtracts them from the primary signal to obtain the corrected EEG data.

35 Claims, 7 Drawing Sheets

ADAPTIVE INTERFERENCE CANCELER FOR EEG MOVEMENT AND EYE ARTIFACTS

This invention was made with Government support under Grant MH43075 awarded by the National Institute of Mental Health, and contract number F41624-94-C-6007 awarded by the Department of the Air Force. The Government has certain rights in the invention.

FIELD OF THE INVENTION

The present invention relates to medical instruments and more particularly to methods for removing contaminants from EEG (electroencephalography) recordings.

BACKGROUND OF THE INVENTION

The brain waves of a human subject provide an electrical signal at the microvolt level. It is possible by connecting removable electrode leads to the scalp of the subject to detect and amplify those faint electrical signals. In the past, those electrical signals were amplified and recorded on a paper strip chart showing an analog wavy line for each recording channel in an EEG (electroencephalograph). EEG has been used for many medical and testing purposes, for example, the testing of auditory, visual, somatosensory and motor systems and testing for pathological brain dysfunction. Presently there are available EEG instruments which can simultaneously detect the faint signals and convert the signals to digital data for recording and analysis.

However, a major problem in obtaining an accurate recording of brain waves has been "movement artifact", which consists of electrical contaminants arising as a consequence of the subject's muscle movements. For example, when a subject moves her head, the muscle action may result in a contaminating electrical signal that will distort or drown out the brain signal. Movement artifacts are caused by the relative movement of the electrode with respect to the scalp. The changes in contact of the electrode on the head result in changes in the impedance and induced potentials at the electrode-scalp interface, producing movement artifacts in the measured EEG. Also head movements can cause the electrode wires to generate a current as they move through the ambient 60 Hz magnetic field, producing "electrode sway artifact".

In addition to movement artifacts, "eye artifact" is another source of electrical contaminants in EEG recordings. When the eyes move or the eyelids blink, electrical potentials can be recorded from electrodes located near the eyes: the "electro-oculogram" or EOG. The eye related potential can also be picked up by EEG electrodes resulting in contaminated EEG signals. Sometimes movement and eye artifacts are present in the measured EEG signal simultaneously.

Because of contamination by movement and eye artifacts, subjects must sit still and restrain eye movements during an EEG recording to minimize head, body or eye movement artifacts. In a clinical situation this is particularly problematic in recording from children, from ambulatory patients, and from patients who are monitored for long periods of time, such as those in intensive care units or in epileptic seizure monitoring diagnostic clinics. Movement and eye artifacts are also a major obstacle hindering recordings of brain electrical activity in laboratory or real world situations, where subjects are performing a task that may involve head, body and eye movements, for instance, working at a computer or flying an airplane. Correction algorithms have been available for eye artifacts [Barlow 1986] but not for movement or compound movement and eye artifacts. Currently data contaminated by head or body movement artifacts, with or without eye artifacts, must be discarded, resulting in prolonged recording sessions or the complete inability to monitor brain activity [Gevins, et al, 1977]. Such discarding of data or marking of contaminated data is mentioned in U.S. Pat. No. 4,171,696 to John and in U.S. Pat. No. 4,736,751 to Gevins, Morgan and Greer.

In U.S. Pat. No. 4,913,152 to Ko et al, magnetoencephalography (MEG) is used to localize and track neuromagnetic signals. In FIG. 4 of the Ko et al patent, auxiliary sensors 24 are used "to help reduce noise contamination". One of the suggested auxiliary sensors is an accelerometer "to detect sensor motion or vibration".

U.S. Pat. No. 4,417,592 to John, for an EEG system, mentions the use of "accelerometer channels, the accelerometer being attached to the patient's head."

These prior patents to Ko et al and to John, incorporated by reference herein, do not disclose the use of an adaptive interference canceler connected to the outputs of the EEG electrodes, accelerometer and eye monitoring channels. The implication in these patents is that if the accelerometer detects movement, the portion of the recording contaminated by such movement would be discarded.

SUMMARY OF THE INVENTION

In accordance with the present invention, there is provided a novel system and method for cancellation of movement artifact, co-existing movement and eye artifacts, or eye artifact in EEG recordings. A reference signal of the movement contaminating the EEG signals is provided by one or more of several alternative means, including an accelerometer or other type of motion detector, and spatial averages of the EEG channels. Preferably an accelerometer or a motion detector detects head motion and determines the starting and ending of movement artifact and the spatial average EEG signal is the reference signal which is used only during such movement artifact. A reference signal of the eye artifact contaminants is provided by eye monitoring channels. An adaptive digital filter removes the contaminants caused by the head, body and eye movements to produce corrected and usable EEG signals.

BRIEF DESCRIPTION OF THE DRAWINGS

The following detailed description should be taken in conjunction with the accompanying drawings, in which.

3

DETAILED DESCRIPTIONS

I. An Adaptive EEG Movement and Eye Artifact Canceler

Figure 1:
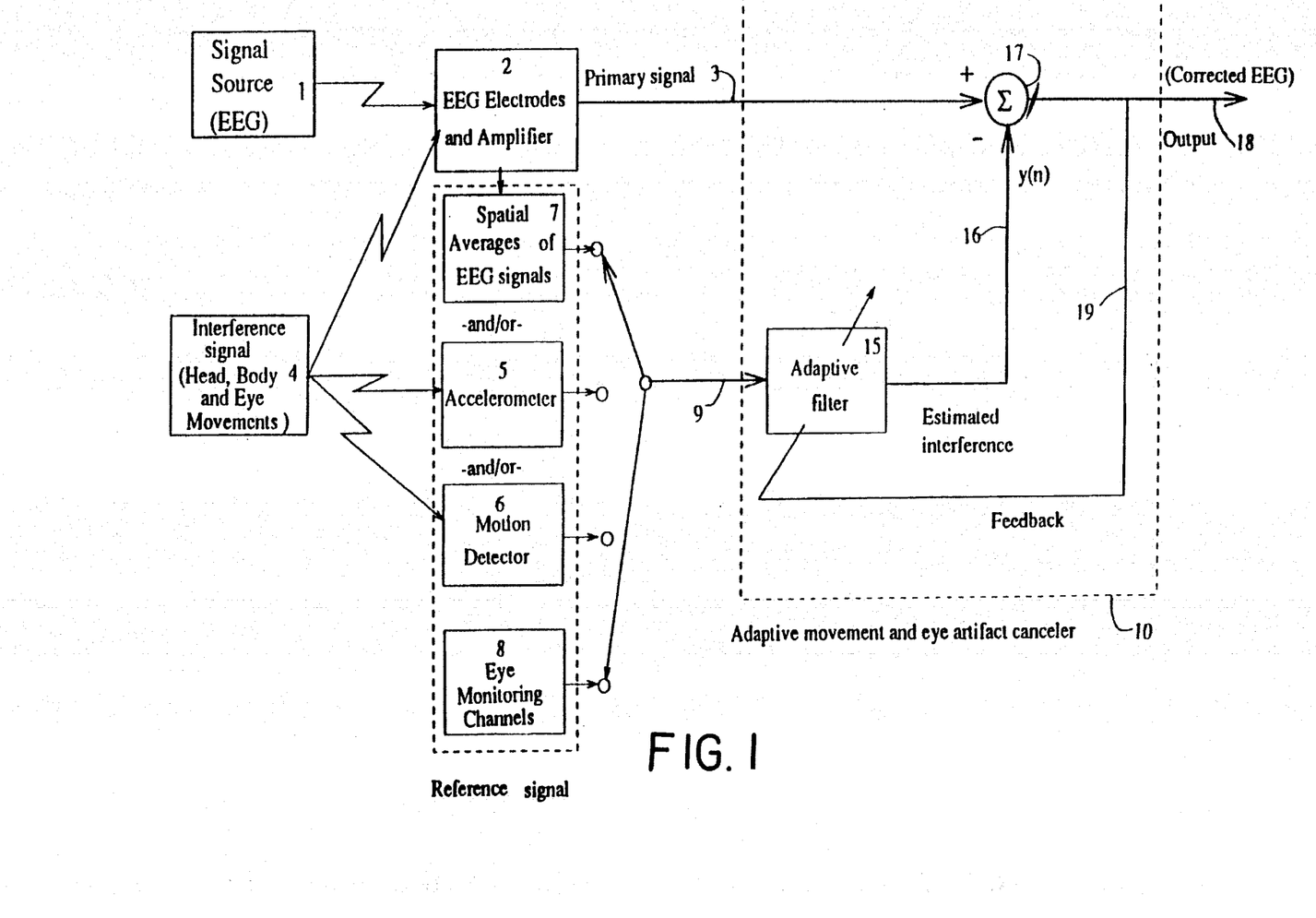
FIGS. 1 and 1A are block diagrams of the adaptive movement and eye artifact canceling method and system of the present invention.

As shown in FIG. 1, the EEG signal source 1 consists of the brain waves of the subject taken at a set of EEG electrodes 2. The brain waves detected at the EEG electrodes are amplified by pre-amplifiers and converted to digital data to produce the primary signal 3. It is essential that the amplifier gains are set in such a way that EEG and artifact reference signals are not saturated. The subject may also have movement and eye artifacts (interference signal 4) which are detected by an accelerometer 5, or other type of motion detector 6, spatial averages of the EEG signal 7 and eye monitoring (EOG) channels 8.

The reference signal 9 and the primary signal 3 are inputs to the adaptive movement and eye artifact canceler 10, described in detail below.

Figure 1A:
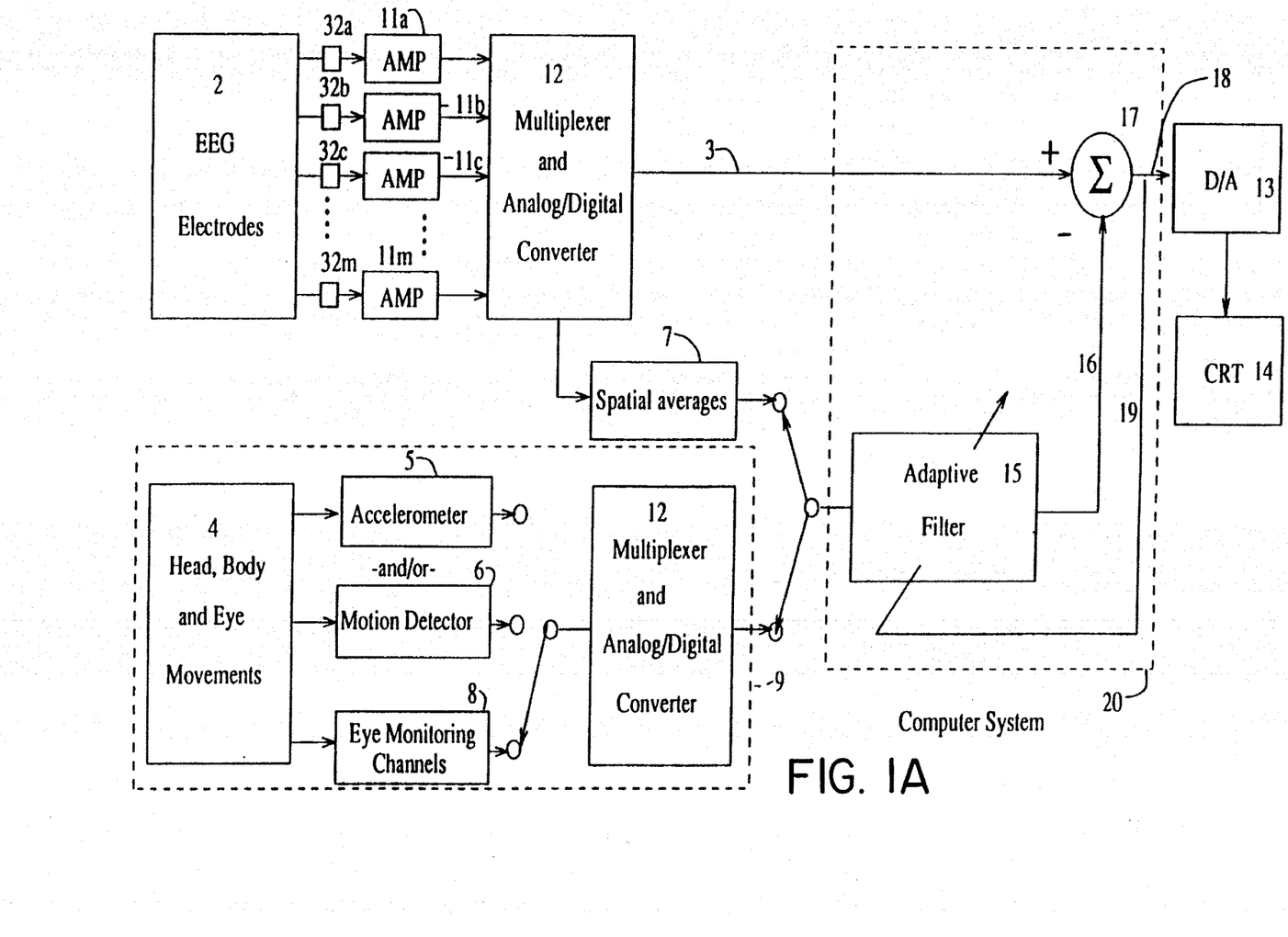

As shown in greater detail in FIG. 1A, a set of EEG electrodes 2 are removablely connected to the scalp of the subject. The set of electrodes 2 consist of EEG electrodes 32a–32m which are electrically connected to low-noise, high-gain pre-amplifiers and amplifiers 11a– 11m. For example, there may be 19, 32, 64 or 128 electrodes, each being part of a channel. The electrodes are preferably in a nylon mesh cap (hat), as shown in U.S. Pat. No. 5,038,782, incorporated by reference herein. The amplifiers 11a–11m are connected to a multiplexer and analog/digital converter 12 ("digitizer"). A suitable amplifier-digitizer is the 128-channel SAM Technology Model SAM/128 with 0.01 to 100 Hz pass-band which digitizes to 16 bits at 256 Hz (SAM Technology, San Francisco, Calif.).

The interference source (head, body and eye movements 4) is monitored by reference signals 9 which are connected to the adaptive artifact canceler 10. The canceler uses an algorithm, described below, which is programmed into, and operated by, a conventional general purpose digital computer or a DSP processor, such as the TMS320C40. The computer used for the experiments in FIGS. 3–6 is a Model ISA-4S6 (ASI, Fremont, Calif.). The output 18 of the computer system 20 is connected to a digital-analog converter 13 (D/A), for example, a video controller and a monitor, for example, a CRT video monitor 14 (video display terminal) or oscilloscope. A recording may also be made on "hard copy" by a printer and the recording saved on a suitable memory means, for later analysis.

This invention offers three options for the movement reference signal including a low-pass filtered spatial average of EEG signals 7, motion detector 6, and accelerometer 5. The eye artifact reference signal 8 can use vertical and horizontal electro-oculogram (EOG) signals which can be recorded by EEG electrodes and EEG amplifiers with reduced gain. Alternatively, an infrared LED or TV camera eye tracking device can be used.

Spatial averages are obtained by averaging the EEG channels using the mean, trimmed mean or median operator. This operation is implemented by a general purpose computer or a DSP processor. Spatial EEG averages are appropriate reference signals because head movement artifacts have an approximately uniform distribution over the head.

4

In situations in which multiple averages are required to provide a complete reference for head movements, the EEG channels can be organized into a few groups and an average calculated within each group. The trimmed mean or median approach is preferred if the EEG data are noisy due to bad electrode contacts or other sources. A zero-phase low-pass filter is applied to the averages to remove frequency components beyond the movement artifact band. The average EEG reference signal should be used judiciously since the averages contain not only movement artifacts, but also EEG signals which are wide spread over the head such as certain pathological low frequency patterns. In these instances, use of an accelerometer or motion detector as a reference signal is preferred.

The spatial EEG averages is preferably used in conjunction with a motion detector or an accelerometer in which case the motion detector or accelerometer are used to determine the onset and offset times of the movement artifact, and the spatial EEG averages are used as the reference signal. The onset and offset times are used, in effect, to turn on and off the canceller so that the canceller is only operative during movement artifact. The use of motion detectors as a movement reference signal is similar to the use of spatial EEG averages. It is preferred that for a motion detector, the movement artifact signal should predominate over other possible signals. A high impedance EEG channel in the pathway from skin to electrode surface is suitable in this regard. Alternatively, the motion detectors may also be low impedance EEG channels which pick up head movement artifacts as well as some unwanted EEG signals, for example, the reference electrodes which are placed on mastoids or earlobes of a subject.

Figure 2:
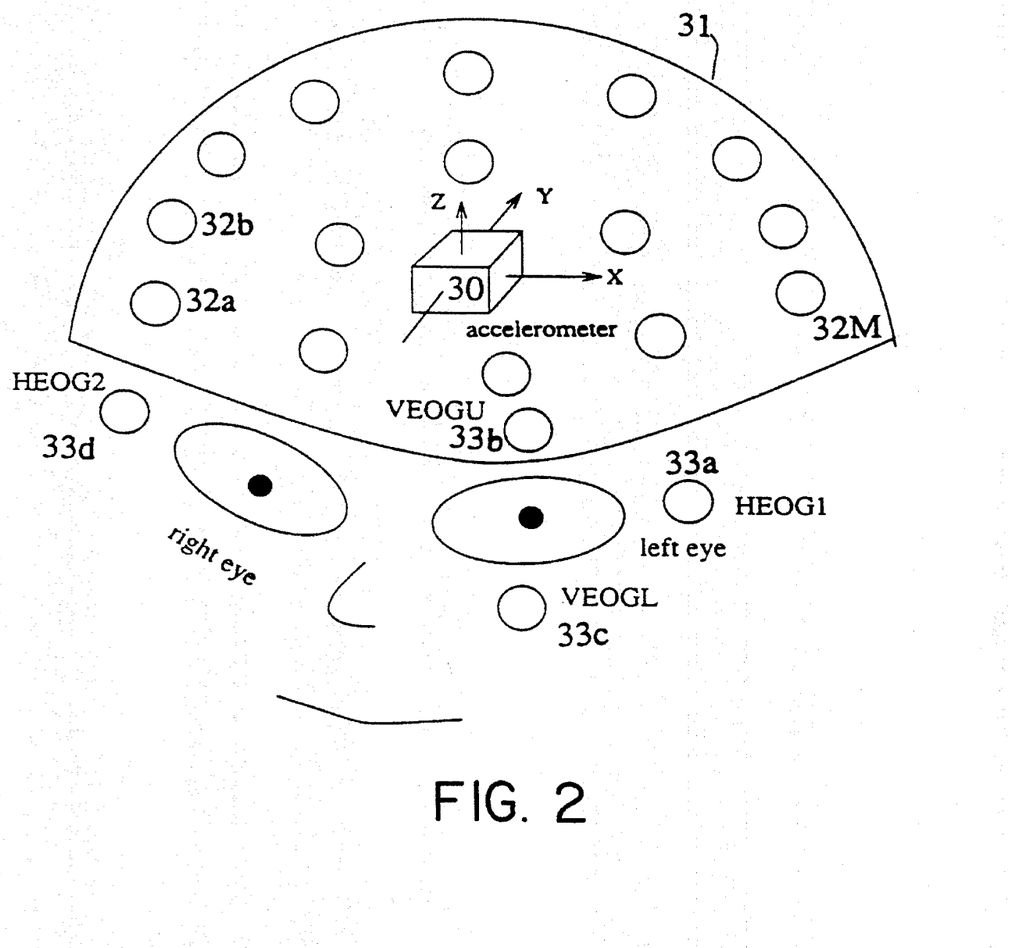
FIG. 2 is a perspective view of an EEG recording hat with an accelerometer, EEG and eye movement electrodes (EOG).

As illustrated in FIG. 2, an accelerometer 30 is generally an electromechanical instrument which measures acceleration. In one embodiment, it can output a multi-channel signal from a multi-axis directional accelerometer, and the measurements are of the x,y,z components of transitional acceleration. Suitable accelerometers may be of the variable-resistance, variable-inductance, piezoelectric, or piezotranslator types. A suitable multi-axis accelerometer is the Model EGA-125-5-D, available from Entran.

In one embodiment, the eye monitoring channels are recorded by electrodes located near the eyes. The vertical component of eye movement is recorded by one electrode above the left eye (VEOGU 33b) and one electrode below the eye (VEOGL 33c). The vertical EOG signal, VEOG, is the difference between the two EOGs or VEOG=VEOGU–VEOGL. Similarly the horizontal EOG (HEOG) is obtained between two electrodes located at outer canthi or HEOG= HEOG1 (left) 33d–HEOG2 (right) 33a. It is also possible to use VEOGU–HEOG1 as the VEOG signal.

As shown in FIG. 2, the EEG recording nylon mesh hat 31 has EEG electrodes 32a–32m, for example, 19–128 electrodes, and an accelerometer 30. The electrodes protrude inside the hat and contact the scalp of the subject and their exterior sides are electrically connected to EEG amplifiers.

An adaptive EEG movement and eye artifact canceler is a multi-channel adaptive filter 15, as is illustrated in FIG. 1. In an adaptive movement and eye artifact canceler, the adaptive filter is used to estimate unknown movement and eye artifacts contained in the recorded EEG, with the estimation being optimized in some sense [Haykin 1991], incorporated by reference herein. The estimated artifact contaminants are subtracted from the measured EEG data.

Let $x_i(n)$ be the measured EEG at the ith electrode at time point n. The data measurement vector $x(n)=[x_1(n),x_2(n), \ldots ,x_M(n)]^T$ is received by M EEG electrodes, which is the desired EEG signal $s(n)$ corrupted by additive movement and eye artifacts $v(n)$. It is assumed that $s(n)$ and $v(n)$ are uncorrelated with each other; that is $$E[s(n)v^T(n-k)]=0, \text{ for all } k$$

where k is the time index increment and E[x] is the expectation value of x.

The composite reference signal vector 9 for both movement and eye artifacts is given by $$u(n)=[u_1(n)u_2(n),\ldots,u_m(u),u_{HEOG}(n),u_{VEOG}(n)]^T$$

where $u_i(n)$ is the ith channel of the movement reference signal and $u_{HEOG}(n)$ and $u_{VEOG}(n)$ are eye channels. The primary EEG signal is the first input to the adaptive artifact canceler. The reference signal u(n) is uncorrelated with the desired signal s(n) but highly correlated with the artifact contaminants u(n) in the primary signal in an unknown way. The reference signal is processed by the Kth order adaptive filter 15 to produce y(n) 16, an estimate of v(n) according to the formula $$y(n) = \sum_{k=0}^{K} w_k^T(n)u(n-k),$$

where $w_k(n) \in R^{(m+2) \times M}$ are the adjustable coefficients of the adaptive filter, with R denoting the real vector space.

We have found that the transfer function between the reference signal and movement artifacts is very close to linear. In this case, K=1 is sufficient for the movement and eye artifact canceler. Then the adaptive filter output y(n) becomes $$y(n)=w^T(n)u(n)$$

The adaptive filter output y(n) is subtracted from the primary signal x(n) by the adder 17. The output 18 of the adaptive movement and eye artifact canceler e(n)=x(n)−y(n) serves as the estimate of the desired clean EEG signal and is a feedback 19 to the adaptive filter.

It is important to note that filter coefficient matrix w(n) is adjusted with time according to the specified optimality criterion. The filter coefficient matrix can be adjusted blockwise or recursively [Haykin 1991]. All adaptive algorithms [Haykin 1991] can be used. Several preferred embodiments will be described.

II. Block Adaptation Algorithms

Block adaptation algorithms assume that data statistics do not change in a given time interval or a data block, and the filter coefficients are calculated using data samples in the block. A general parametric model characterizing the dynamic EEG system is given as follows.

$$A(q)x(n) = \frac{B(q)}{F(q)} u(n) + \frac{C(q)}{D(q)} e(n), \quad (1)$$

where x(n) is the observed EEG signal; u(n) is the artifact reference signal, and e(n) is a random noise with unit variance. A(q),B(q)/F(q),C(q)/D(q) denote the transfer operators determined by the rational model parameters. For example, y(n)=B(q)/F(q)u(n) is equivalent to y(n)+f$_1$y(n−1)+f$_2$y(n−2)+ ... +f$_{n_f}$y(n−n$_f$)=b$_0$ u(n)+b$_1$u(n−1)+ b$_2$u(n−2)+ ... +b$_{n_b}$u(n−n$_b$), where n$_b$ and n$_f$ denote the orders of the model. y(n) is an estimate of the artifact contaminants, and it is subtracted from the x(n) to obtain the corrected EEG signal. Almost all parametric models are special cases of this general model including ARX (autoregressive with external input), ARMAX (autoregressive and moving average with external input), Box-Jenkins, ARMA (autoregressive and moving average), Wiener filters, Linear Predictors. When a specific model, e.g. ARX, is selected, a block algorithm is used to calculate the filter coefficients. The detailed discussions on model or filter coefficient calculation can be found in [Ljung 1987] and [Haykin 1991].

When the data block is chosen to cover all the available data samples, block adaptation filters reduce to nonadaptive filters, where filter coefficients are calculated once and do not change with time. Because EEG signals and artifact contaminants are stochastic processes, adaptive algorithms are preferred though nonadaptive filters can also be used.

III. Recursive Adaptation Algorithms

In recursive adaptation algorithms, filter coefficients are adjusted for every new data sample. Recursive algorithms are suitable for fast time-variant signals or for real-time artifact canceling systems. Examples of recursive algorithms include the Recursive Least Squares (RLS), the Least Mean Square (LMS), Kahnan filters, and the exponentially weighted RLS (EWRLS). The parametric models in section II can also be updated recursively, but they are seldom used in a real-time system because of the complexity of the algorithms. Two preferred embodiments of recursive adaptive filters are the Least Mean Square (LMS) and the Exponentially Weighted Recursive Least Squares (EWRLS) methods due to their simplicity in implementation.

III-a. The LMS Algorithm

One approach to adaptive filtering is to select the new weight matrix w(n+1) so as to descend on the error surface in the direction of the gradient of the error. The LMS algorithm utilizes instantaneous estimates of the gradient from the observed data for error minimization. The advantage of the LMS algorithm is its simplicity; it does not require measurements of the pertinent correlation nor does it require matrix inversion. The recursive relations for the LMS are given as follows:

$$w(n)=w(n-1)+\mu u(n-1)*e^T(n-1) \quad (2)$$

$$e(n)=x(n)-w^T(n)*u(n) \quad (3)$$

The gain constant μ controls the convergence characteristics of the LMS algorithm. It has been shown that the convergence of the LMS algorithm is guaranteed provided the following condition is satisfied.

$$0 < \mu < \frac{2}{\delta_{max}} \quad (4)$$

where $\delta_{max}$ is the largest eigenvalue of the correlation matrix $R_u$ of the reference signal. The convergence rate of the LMS algorithm depends on the eigenstructure of $R_u$. When the eigenvalues are widely spread, convergence can be very slow and other algorithms with better convergence characteristics should be considered, such as the EWRLS algorithm.

III-b. The EWRLS Algorithm

The EWRLS algorithm minimizes the exponentially weighted sum of the adaptive filter output in the 2-norm sense, or it minimizes the objective function $$J(n) = \sum_{m=-\infty}^{n} \lambda^{m-n} e^T(n)e(n) \quad (5)$$

where λ is the forgetting factor. Because the reference signal is uncorrelated to the desired clean EEG signal and is highly correlated to the movement and eye contamination, minimizing the norm of e(n) is equivalent to maximizing the output signal-to-noise ratio of the system. The recursive relations of the EWRLS method are given as follows:

$$k(n) = \frac{\lambda^{-1}v(n)}{1+\lambda^{-1}u^T(n)v(n)} \quad (7)$$

$$\alpha(n)=x(n)-w^T(n-1)u(n) \quad (8)$$

$$w(n)=w(n-1)+k(n)\alpha^T(n) \quad (9)$$

$$P(n)=\lambda^{-1}P(n-1)-\lambda^{-1}k(n)v^T(n) \quad (10)$$

where P(n) is the inverse of the correlation matrix of the reference signal. The w(n) represents the least squares solution at each instant n and is optimal in a deterministic sense. Convergence to the statistically optimal weight matrix is often faster than that obtained using the LMS algorithm.

IV. Examples

Figure 3A:
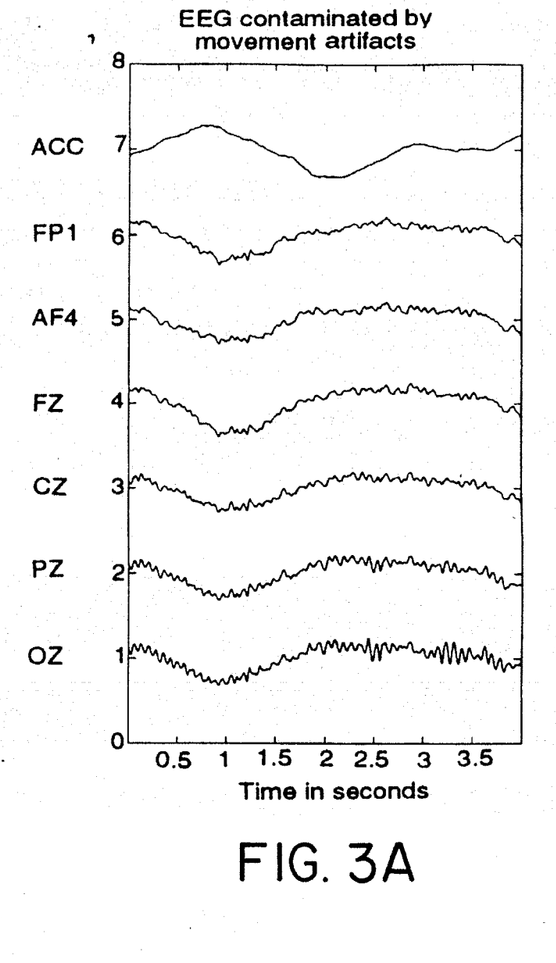
FIG. 3 is a graph showing the original EEG data contaminated by movement artifacts (leg plot) and the same data after movement artifacts have been removed (right plot). The accelerometer output (labelled ACC) was used as the reference signal.
Figure 3B:
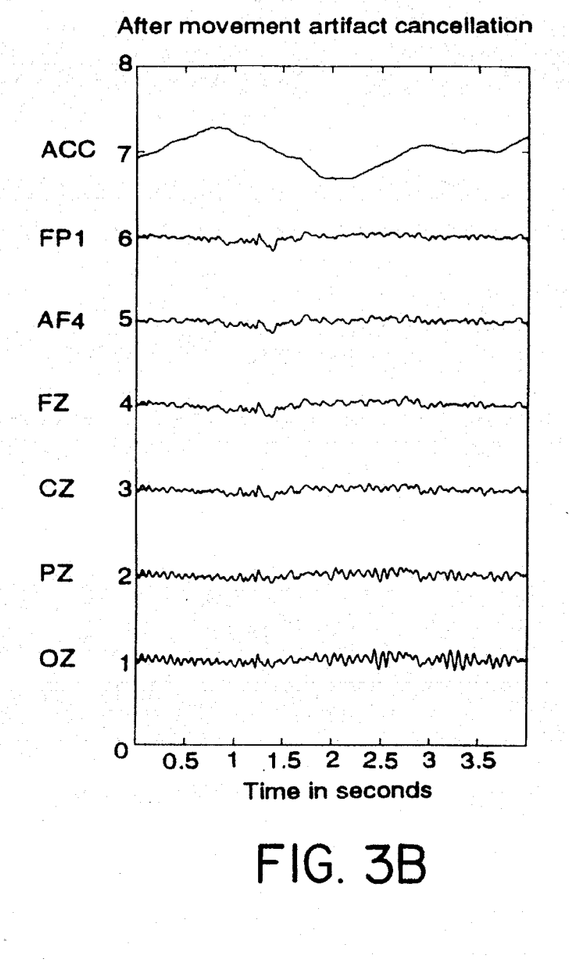
Figure 4A:
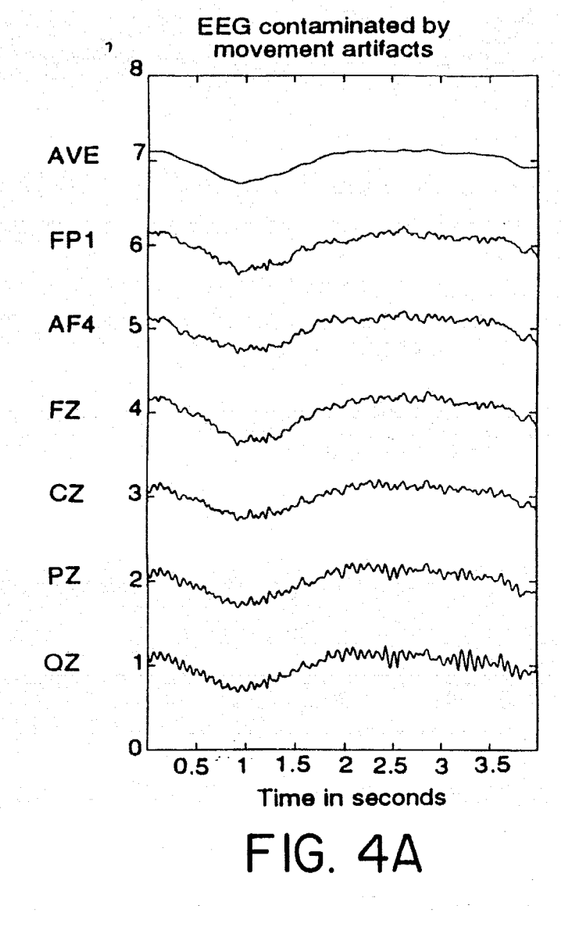
FIG. 4 is a graph showing the original EEG data contaminated by movement artifacts (left plot) and the same data after movement artifacts have been removed (right plot). The spatial averages of the EEG channels (labeled AVE) was used as the reference signal.
Figure 4B:
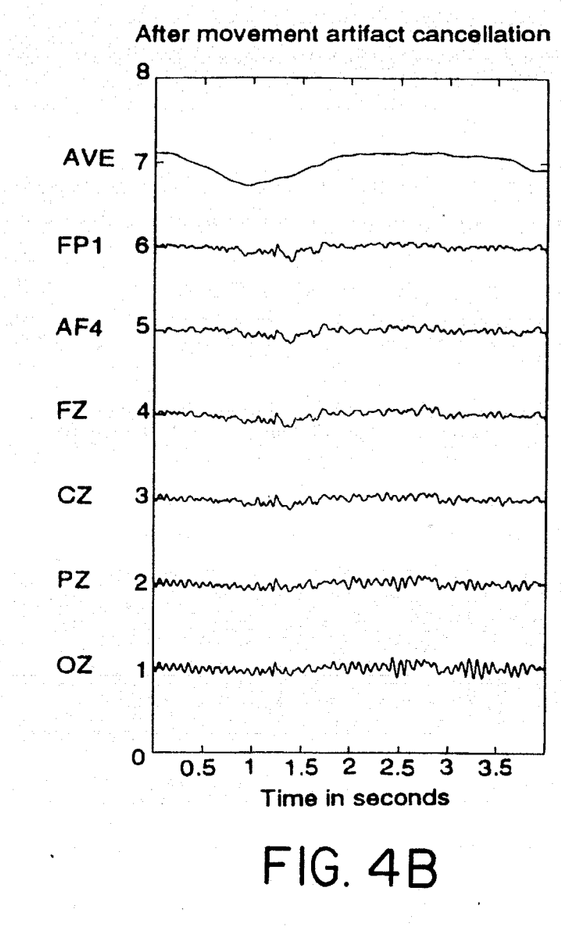
Figure 5A:
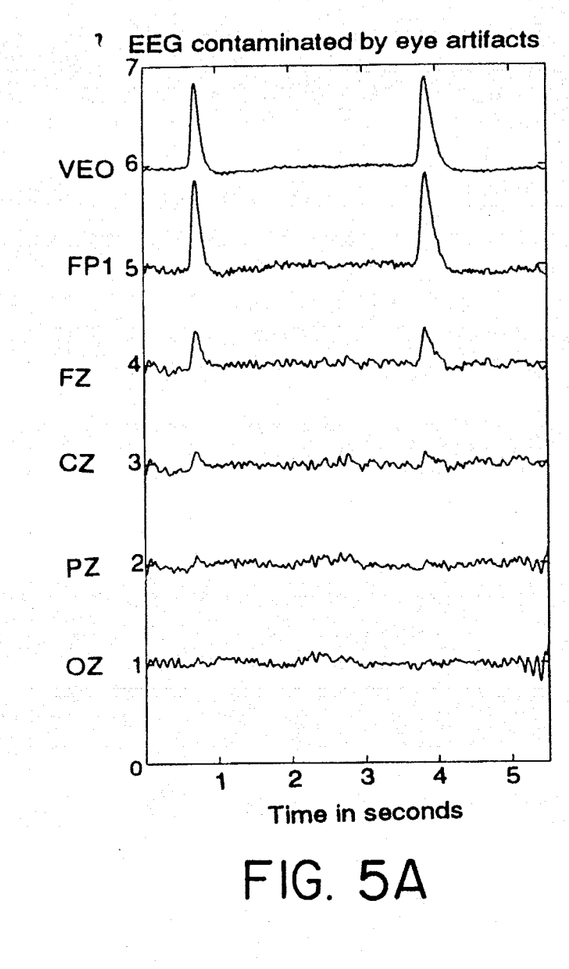
FIG. 5 is a graph showing the original EEG data contaminated by eye artifacts (left plot) and the same data after eye artifacts have been removed (right plot). Eye channels (VEOG and HEOG) were used as reference signals.
Figure 5B:
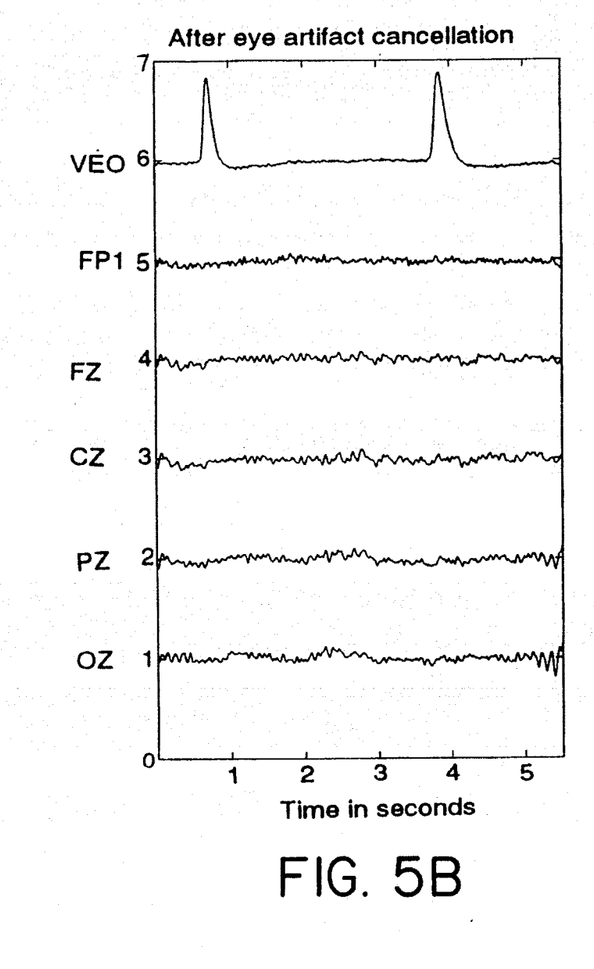
Figure 6A:
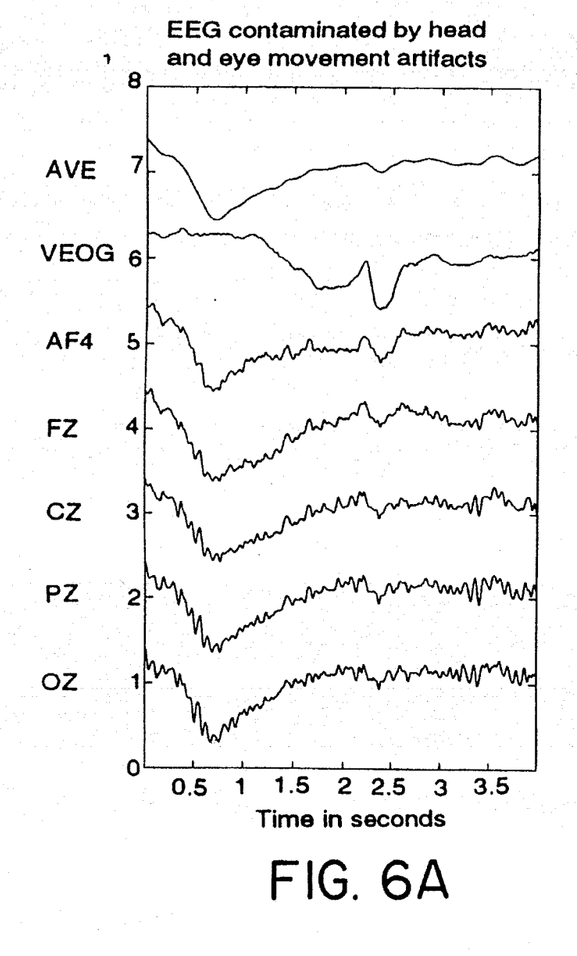
FIG. 6 is a graph showing the original EEG data contaminated by movement and eye artifacts (left plot) and the same data after the artifacts have been removed (right plot). The spatial averages of the EEG channels (labeled AVE), VEOG and HEOG (not plotted) channels were used as the reference signals.
Figure 6B:
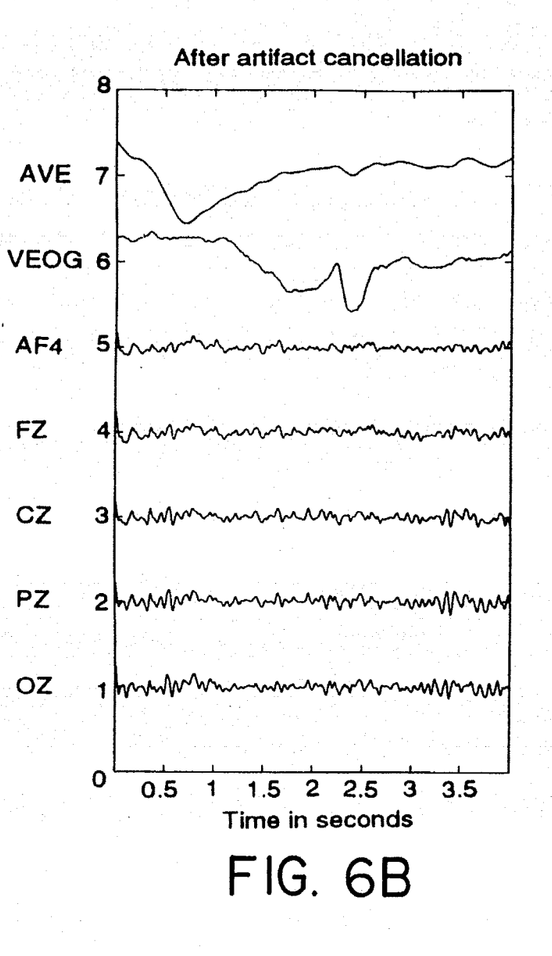

FIG. 3 shows EEG data recorded from a subject who moved her head in different directions and was allowed to blink freely. Data was collected on 27 EEG channels (of which 6 are shown FP1 through OZ) and 3 accelerometer channels (of which one is shown, ACC). The recorded EEG signal is corrupted by movement artifacts which can be recognized by a low frequency component which varies in time with the accelerometer outputs( left side). FIG. 3 (right side) shows the same data after the adaptive filter was applied. FIG. 4 (left side) shows the same six contaminated EEG channels as in FIG. 3 (left side). The top trace (AVE) shows the median average of the all 27 EEG channels. FIG. 4 (right side) shows the same data after the adaptive filter was applied to correct the contaminated EEG data, FIG. 5 (left side) shows a segment of data corrupted by eye blinks; the same data after eye artifacts have been filtered are shown on the right side, FIG. 6 (left side) shows a segment of data corrupted by compound artifacts due to eye and head movements; the same data after artifacts have been filtered are shown on the right side.

REFERENCES

Barlow, J. S. "Artifact processing (rejection and reduction) in EEG data processing," In F. H. Lopes da Silva, W. Storm van Leeuwen, A. Remond (Eds.) *Handbook of Electroencephalography and Clinical Neurophysiology*, Vol. 2. Elsevier: Amsterdam, pp. 15–65, 1986.

Simon Haykin, *Adaptive Filter Theory*, Prentice Hall, Englewood Cliffs, N.J. 07632, 1991.

Lennart Ljung, *System Identification: Theory for the user*, Prentice Hall, Englewood Cliffs, N.J. 07632, 1987.

A. S. Gevins, et al, "On-line computer rejection of EEG artifact," *Elect. & Clin. Neurophysiology*, vol. 42, pp267–274, 1977.

We claim:

1. An EEG (electroencephalograph) system comprising:
  (a) a plurality of EEG electrode means adapted to be removably connected to the scalp of a subject to detect the subject's brain waves;
  (b) amplification means connected to the EEG electrode means to amplify the detected brain waves and produce an amplified signal output for each EEG electrode means;
  (c) a three-axis translation accelerometer adapted to be removably positioned on the head of the subject to detect the subject's head movement, the accelerometer producing at least one signal output indicative of the head movements;
  (d) an interference canceler connected to the outputs of the amplification means and the accelerometer signal output, the canceler comprising a filter having an output and an adder connected to the output of the filter and the amplification means, the adder producing corrected and usable EEG signals.

2. An EEG system as in claim 1 and further comprising an eye movement sensor means adapted to be removably connected proximate an eye of the subject to generate an eye movement reference signal which is an input to the filter.

3. An EEG system as in claim 1 wherein the filter uses an algorithm embodied in a software program executed on a digital computer system or embodied in a digital hardware circuit.

4. An EEG system as in claim 3 wherein the filter is an adaptive filter having a coefficient matrix which is adjusted with time according to a Least Mean Squares (LMS) algorithm.

5. An EEG system as in claim 4 wherein the filter is an adaptive filter having a filter coefficient matrix which is adjusted with time according to an Exponentially Weighted Recursive Least Squares (EWRLS) algorithm or a Recursive Least Squares (RLS) algorithm.

6. An EEG system as in claim 3 wherein the filter uses a block adaptive filter algorithm selected from the group of autoregressive with external input (ARX), autoregressive and moving average with external input (ARMAX), Wiener filters, Kalman filters, Linear Predictors, autoregressive and moving average (ARMA) and Box-Jenkins model.

7. An EEG system as in claim 1 wherein the filter is an analog hardware circuit.

8. An EEG system as in claim 1 wherein the filter is a non-adaptive filter.

9. An EEG (electroencephalograph) system comprising:
  (a) a plurality of EEG electrode means adapted to be removably connected to the scalp of a subject to detect the subject's brain waves;
  (b) amplification means connected to the EEG electrode means to amplify the detected brain waves and produce an amplified signal output for each EEG electrode means;
  (c) signal averaging means to combine and average at least some of the amplified signal outputs to generate a spatial average EEG signal as a head and body reference signal; and
  (d) an interference canceler connected to the outputs of the amplification means and the signal averaging means, the canceler comprising a filter having an output, and an adder connected to the output of the filter and the amplification means, the adder producing corrected and usable EEG signals.

10. An EEG system as in claim 9 and further including an accelerometer or movement detector adapted to be removably positioned on the head of the subject to detect the subject's head movements, the accelerometer or movement detector generating at least one signal indicative of head movements, which signal is used to determine the starting and ending of the head movements, and means to operate the canceler only during said determined head movements.

11. An EEG system as in claim 11 wherein an accelerometer is positioned on the subject's head and the accelerometer is a three-axis translational accelerometer.

12. An EEG system as in claim 9 wherein the filter is an adaptive filter.

13. An EEG system as in claim 12 wherein the adaptive filter comprises a filter coefficient matrix which is adjusted with time according to a Least Mean Squares (LMS) algorithm.

14. An EEG system as in claim 12 wherein the adaptive filter comprises a filter coefficient matrix which is adjusted with time according to an Exponentially Weighted Recursive Least Squares (EWRLS) algorithm or Recursive Least Squares (RLS) algorithm.

15. An EEG system as in claim 9 wherein the filter is an algorithm embodied in a software program executed on a digital computer system or embodied in a digital hardware circuit.

16. An EEG system as in claim 9 wherein the filter is an analog hardware circuit.

17. An EEG system as in claim 9 wherein the filter comprises a block adaptive filter algorithm selected from the group of autoregressive with external input (ARX), autoregressive and moving average with external input (ARMAX), Wiener filters, Kalman filters, Linear Predictors, autoregressive and moving average (ARMA) and Box-Jenkins model.

18. An EEG system as in claim 9 and further comprising an eye movement sensor means adapted to be removably connected proximate an eye of the subject to generate an eye movement reference signal which is an input to the filter.

19. An EEG system as in claim 9 wherein the filter is a non-adaptive filter.

20. An EEG (electroencephalograph) method comprising the steps of:
   (a) connecting a plurality of EEG electrodes to the scalp of a subject to detect the subject's brain waves;
   (b) amplifying the subject's brain waves using amplification means connected to the EEG electrodes to produce an amplified signal output for each EEG electrode;
   (c) connecting a three-axis translation on the head of the subject to detect the subject's head movements, the accelerator producing at least one reference signal output indicative of the head movements;
   (d) using an interference canceler to produce corrected EEG signals, the canceler being connected to the output of the amplification means and to the reference signal, the canceler comprising a filter having an input connected to the output of the reference signal and having an output, and an adder connected to the output of the filter and the amplification means, the adder producing corrected and usable EEG signals.

21. An EEG method as in claim 20 wherein the filter is an adaptive filter executed in an algorithm embodied in a software program executed on a digital computer system or embodied in a digital hardware circuit.

22. An EEG method as in claim 21 wherein the adaptive filter comprises a filter coefficient matrix which is adjusted with time according to a Least Means Squares (LMS) algorithm.

23. An EEG method as in claim 21 wherein the adaptive filter comprises a filter coefficient matrix which is adjusted with time according to an Exponentially Weighted Recursive Least Squares (EWRLS) algorithm or a Recursive Least Squares (LRS) algorithm.

24. An EEG method as in claim 20 wherein the filter comprises a block adaptive filter algorithm selected from the group of autoregressive with external input (ARX), autoregressive and moving average with external input (ARMAX), Wiener filters, Kalman filters, Linear Predictors, autoregressive and moving average (ARMA) and Box-Jenkins model.

25. An EEG method as in claim 20 and further including the step of generating an eye movement reference signal as an input to the filter, the eye movement reference signal being generated from an eye movement sensor removably connected proximate an eye of the subject.

26. An EEG method as in claim 20 wherein the filter is a non-adaptive filter.

27. An EEG (electroencephalograph) method comprising the steps of:
   (a) connecting a plurality of EEG electrodes to the scalp of a subject to detect the subject's brain waves;
   (b) analyzing the subject's brain waves using amplification means connected to the EEG electrodes to produce an amplified signal output for each EEG electrode;
   (c) combining and averaging at least some of the amplified signal outputs and thereby generating a spatial average EEG signal as a head and body reference signal; and
   (d) using an interference canceler to produce corrected EEG signals, the canceler being connected to the output of the amplification means and to the reference signal, the canceler comprising a filter having an input connected to the reference signal and having an output, and an adder connected to the output of the filter and the amplification means, the adder producing corrected and usable EEG signals.

28. An EEG method as in claim 27 and further comprising removably connecting an accelerometer or movement detector on the head of the subject to detect head movements, the accelerometer or movement detector generating at least one signal indicative of head movements, using the head movement signal to determine the starting and ending of head movements, and operating the interference canceler only during said determined head movements.

29. An EEG method as in claim 28 wherein an accelerometer is connected on the head of the subject and the accelerometer is a three-axis translational accelerometer.

30. An EEG method as in claim 27 wherein the filter is an adaptive filter which is an algorithm embodied in a software program executed on a digital computer system or embodied in a digital hardware circuit.

31. An EEG method as in claim 27 wherein the filter is an analog hardware circuit.

32. An EEG method as in claim 27 wherein the filter is an adaptive filter having a filter coefficient matrix which is adjusted with time according to a Least Mean Squares (LMS) algorithm.

33. An EEG method as in claim 27 wherein the filter is an adaptive filter having a filter coefficient matrix which is adjusted with time according to an Exponentially Weighted Recursive Least Squares (EWRLS) algorithm or a Recursive Least Squares (RLS) algorithm.

34. An EEG method as in claim 27 wherein the filter uses a block adaptive filter algorithm selected from the group of autoregressive with external input (ARX), autoregressive and moving average with external input (ARMAX), Wiener filters, Kalman filters, Linear Predictors, autoregressive and moving average (ARMA) and Box-Jenkins model.

35. An EEG method as in claim 27 wherein the filter is a non-adaptive filter.

* * * * *